United States Patent
Dahanayake et al.

(10) Patent No.: US 9,035,104 B2
(45) Date of Patent: May 19, 2015

(54) PROCESS FOR MAKING POLYGLYCEROL ETHERS OF FATTY ALCOHOLS

(75) Inventors: Manilal S. Dahanayake, Princeton Junction, NJ (US); Andrew Douglass, San Ramon, CA (US); Robert Lee Reierson, Princeton Junction, NJ (US)

(73) Assignee: Rhodia Operations, Aubervilliers (FR)

( * ) Notice: Subject to any disclaimer, the term of this patent is extended or adjusted under 35 U.S.C. 154(b) by 151 days.

(21) Appl. No.: 13/374,192

(22) Filed: Dec. 15, 2011

(65) Prior Publication Data

US 2012/0215031 A1 Aug. 23, 2012

Related U.S. Application Data

(60) Provisional application No. 61/459,673, filed on Dec. 16, 2010.

(51) Int. Cl.
| | | |
|---|---|---|
| *C07C 43/10* | (2006.01) | |
| *C07C 41/09* | (2006.01) | |
| *C08G 65/34* | (2006.01) | |

(52) U.S. Cl.
CPC ............... *C07C 41/09* (2013.01); *C08G 65/34* (2013.01)

(58) Field of Classification Search
CPC ....................................................... C07C 43/10
USPC .......................................................... 568/619
See application file for complete search history.

(56) References Cited

U.S. PATENT DOCUMENTS

| | | |
|---|---|---|
| 4,788,345 A | 11/1988 | Sebag et al. |
| 5,512,666 A | 4/1996 | McCurry, Jr. et al. |
| 2002/0035238 A1 | 3/2002 | Nakamura et al. |
| 2008/0306211 A1 | 12/2008 | Lemke et al. |
| 2010/0062960 A1 | 3/2010 | Sakanishi |

FOREIGN PATENT DOCUMENTS

| | | |
|---|---|---|
| EP | 1785410 A1 | 5/2007 |
| WO | WO-2007092407 * | 8/2007 |
| WO | WO2007092407 A2 | 8/2007 |

OTHER PUBLICATIONS

Glycerine Producers' Association, Chemical Properties and Derivatives of Glycerine, 1965, NY.

* cited by examiner

*Primary Examiner* — Yong Chu
*Assistant Examiner* — Sonya Wright
(74) *Attorney, Agent, or Firm* — Xuping Fu

(57) ABSTRACT

Disclosed are processes relating to the production of polyglycerol ethers of fatty alcohols, in particular, one step process using fatty alcohol and glycerine to synthesize polyglycerides of fatty alcohols will provide a 100% renewable surfactant that is cost effective efficient and CMR free. The synthetic methods mentioned in prior art uses hazardous chemicals as glycidyl ethers, epichlorohydrin that are listed as CMR and known carcinogens and hazardous to handle.

19 Claims, No Drawings

PROCESS FOR MAKING POLYGLYCEROL ETHERS OF FATTY ALCOHOLS

CROSS-REFERENCE TO RELATED APPLICATION

This application claims the benefit of U.S. Provisional Application Ser. No. 61/459,673, filed Dec. 16, 2010, herein incorporated by reference.

FIELD OF INVENTION

This invention relates to polyglycerol ethers and, in particular, to processes relating to the production of polyglycerol ethers of fatty alcohols.

BACKGROUND OF THE INVENTION

Polyglycerol (or otherwise hereinafter referred to as "polyglyceride") monoethers such as polyglycerol monoalkyl ethers have been produced according to various processes utilizing for example chlorohydrin or a chlorohydrin-based reactant. In some cases, glycerol ethers can be prepared from glycidol, epichlorohydrin or a glycidol ether treatment with an alcohol or phenol and catalyzed by an acid or alkali.

As one example, a process can include adding epichlorohydrin to an alcohol under basic conditions. Dehydrochlorination and ring-closing are carried out under these basic conditions, and ring-opening is carried out with a diluted sulfuric acid. This procedure is repeated until a target degree of polymerization is obtained. This process of making polyglycerol monoethers, however, is not desirable if the polyglycerol monoethers are to be utilized in cosmetics, food, detergents or the like, because the finished product may contain undesired chlorine compounds. There are also concerns about the safety of chlorohydrin or a chlorohydrin-based compounds as, for example, the use of epichlorohydrin is unsafe and is classified under CMR (Carcinogenic, Mutagenic or Toxic to Reproduction).

In addition, in order to produce a product having a high degree of polymerization, use of the above-referenced process can involve complicated reaction steps and a high relative cost. The reason is because a product having a single degree of polymerization alone is obtained according to the process described-above.

As another example, a process can include adding glycidol to a compound having a phenolic hydroxyl group, such as an alkylphenol, which has a high reactivity associated with the phenolic hydroxyl group. Similar to epichlorohydrin the use of glycidol is unsafe and requires special precautions in handling and transportation. Moreover, glycidol is reasonably anticipated to be a human carcinogen and, as such, it is not suitable and/or desirable to use in home and personal care applications, cosmetics, foodstuffs, detergents, cleaners, etc. and the like.

Yet another process includes reacting an aliphatic alcohol with a glycidyl ester, such as glycidyl acetate, in the presence of an alkali metal catalyst. Yes another process includes reacting an organic hydroxyl compound with benzyl glycidyl ether in the presence of a phase-transfer catalyst. Such processes, however, carry out protection and deprotection of glycidol and are thereby complicated in procedures, although target compounds are obtained. In addition, these processes are not chemically and industrially safe when an acid hydride, for example, is used as a protecting reagent, because an acid formed in the system may invite an abnormal reaction.

Polyglycerol monoethers are known substances but have not been generally used, because they contain large amounts of impurities such as polyglycerols, dialkyl components, residual amounts of epoxide containing compounds such as glycidol, chlorohydrin, dichlorohydrin and related compounds, which may be human carcinogens and/or classified under CMR, and are also costly to produce.

Analogous compounds such as polyglycerol mono(fatty acid) esters and polyoxyethylene monoalkyl ethers have been used in cosmetics, home and personal care applications, detergents, etc. However, use of polyglycerol fatty acid esters, for example, are limited because of its insufficient in resistance to hydrolysis, to salts, and to acids. Polyoxyethylene monoalkyl ethers may yield formaldehyde and are low in water-solubility. Such formaldehyde has been perceived as a problem. Accordingly, demands of the market have been made on replacements of these compounds.

Accordingly, there is a need for an improved process for making polyglycerol alkyl ethers without the drawbacks as mentioned above.

SUMMARY OF INVENTION

This invention relates to a direct method for preparing alkyl mono and polyglycerides or polyglycerol which, in one embodiment, includes the reaction of glycerin and/or polyglycerol and one or more fatty alcohols in the presence of a distillable co-solvent and/or emulsifier and a catalyst. In some embodiments, the fatty alcohol having from about 8 to about 22 carbon atoms. The process described herein yields alkyl glycerides useful in replacing most of the linear, branched and alkylphenol ethoxylates and their derivatives used in various industrial, detergent, paints coatings agrochemical pharmaceutical drugs, foodstuffs, cosmetics and biochemistry.

An alkyl glyceride made by the processes according to the invention exhibits improved yield, composition, surface activity and/or is free of salts and CMR by-products as compared to alkyl ether glycerides made from using epichlorohydrin or glycydol and fatty alcohols.

Described herein are high-quality polyglycerol monoethers represented by following formula (I):

$$R_1O-(C_3H_6O_2)_n-H \qquad (I)$$

wherein $R_1$ represents an alcohol residue having from about 1 to 40 carbon atoms, typically from about 1 to 30 carbon atoms, more typically from about 1 to 25 carbon atoms; and "n" is an average number of moles of added glycerol units and represents a number of 2 or more. Another object of the present invention is to provide a process for producing polyglycerol monoethers of formula (I) without the use of hazardous CMRs.

Also described herein are high-quality polyglycerol polyethers generally represented by following formula (II):

$$R_1O-(C_3H_5O_2R_2)_n-H \qquad (II)$$

wherein $R_1$ and $R_2$ each individually represents an alcohol residue having from about 1 to 40 carbon atoms, typically from about 1 to 30 carbon atoms, more typically from about 1 to about 25 carbon atoms; and "n" is an average number of moles of added glycerol units and represents a number of 2 or more. Another object of the present invention is to provide a process for producing polyglycerol polyethers of formula (II) without the use of hazardous CMRs.

The invention in one aspect is a process for preparing a polyglycerol ether of fatty alcohol comprising the steps of: a) contacting a fatty alcohol with glycerine, polyglycerine or polyglycerol, in the presence of an: (i) acid/alkaline catalyst, (ii) a solvent, and (iii) a short chain alcohol, emulsifier or a combination thereof. In one embodiment, a distillate of the short chain alcohol, emulsifier or combination thereof is monitored and process or reaction halted after the appearance of said distillate. In another embodiment, the process is halted after a sample of the reaction mixture is mixed in water to from an aqueous dispersion, and thereafter foaming appears in the aqueous dispersion.

The invention in another aspect is a process for preparing a polyglycerol polyether of formula I:

  (1)

wherein $R_1$ is individually a $C_8$-$C_{22}$ alkyl group or hydrogen and —n— is an integer greater than 1, the process comprising the steps of: a) contacting a fatty alcohol with glycerine, in the presence of an: (i) acid/alkaline catalyst, (ii) a solvent, and (iii) a short chain alcohol or emulsifier or both; b) monitoring the distillate of the short chain alcohol or emulsifier or both. In one embodiment, distillation is carried out at reduced pressure and, optionally, under inert gas.

In yet another aspect, the invention is a process for preparing a polyglycerol polyether of formula II:

  (II)

wherein $R_1$ and $R_2$ are individually a $C_8$-$C_{22}$ alkyl group or hydrogen and —n— is an integer greater than 1, the process comprising the steps of: a) contacting a fatty alcohol with glycerine, in the presence of an: (i) acid/alkaline catalyst, (ii) a solvent, and (iii) a short chain alcohol or emulsifier or both; b) monitoring the distillate of the short chain alcohol or emulsifier or both. In one embodiment, distillation is carried out at reduced pressure and, optionally, under inert gas.

DETAILED DESCRIPTION OF INVENTION

It should be understood that the foregoing description is only illustrative of the present invention. Various alternatives in the order of additions, conditions for the reaction; temperature, pressure, distillation rates, use of catalyst (e.g., acidic, basic, metallic and the like) can be devised without departing from the invention. Accordingly, the present invention is intended to embrace all such alternatives, modifications and variances.

In one embodiment, described herein are synthetic methods using one step process to synthesize alkylpolyglycerides or alylpolyglycerol. Such processes can provide a low cost route to green surfactant with renewable carbons. The compounds prepared using the processes described herein can easily be converted to anionic cationic and zwitterionic surfactants with broad utility. Some methods described herein comprise alkylation of glycerin with fatty alcohols in making polyglyceride ethers of alcohols.

In one embodiment, the process for making alkyl ether polyglycerides comprises reacting with glycerol and/or glycerin is in the presence of an acid/alkaline catalyst and a mutual solvent to form a product of alkyl ether glyceride at a certain temperature and reduced pressure. The method makes use of a compatiblizer such as a short chain alcohol, an emulsifier, a mutual solvent (such as, for example, dibasic esters) or any combination thereof which are typically used in small amount in the reaction mixture with an acidic or alkaline catalyst (such as an inorganic acid/organic acid). An alcohol and the glycerin or the polyglycerin is added to reaction mixture. The mixture is heated under reduced pressure and the distillate is monitored. In one embodiment, when a distillate appears, the reaction is halted. The order of addition for these reactants and the catalyst can be changed in optimizing the out come.

The invention in one aspect is a process for preparing a polyglycerol ether of fatty alcohol comprising the steps of: a) contacting a fatty alcohol with glycerine, polyglycerine or polyglycerol, in the presence of an: (i) acid/alkaline catalyst, (ii) a solvent, and (iii) a short chain alcohol, emulsifier or a combination thereof. In one embodiment, a distillate of the short chain alcohol, emulsifier or combination thereof is monitored and process or reaction halted after the appearance of said distillate. In another embodiment, the process is halted after a sample of the reaction mixture is mixed in water to from an aqueous dispersion, and thereafter foaming appears in the aqueous dispersion.

The invention in another aspect is a process for preparing a polyglycerol polyether of formula I:

  (1)

wherein $R_1$ is individually a $C_8$-$C_{22}$ alkyl group or hydrogen and —n— is an integer greater than 1, the process comprising the steps of: a) contacting a fatty alcohol with glycerine, in the presence of an: (i) acid/alkaline catalyst, (ii) a solvent, and (iii) a short chain alcohol or emulsifier or both; b) monitoring the distillate of the a short chain alcohol or emulsifier or both. In one embodiment, distillation is carried out at reduced pressure and, optionally, under inert gas.

In yet another aspect, the invention is a process for preparing a polyglycerol polyether of formula II:

  (II)

wherein $R_1$ and $R_2$ are individually a $C_8$-$C_{22}$ alkyl group or hydrogen and —n— is an integer greater than 1, the process comprising the steps of: a) contacting a fatty alcohol with glycerine, in the presence of an: (i) acid/alkaline catalyst, (ii) a solvent, and (iii) a short chain alcohol or emulsifier or both; b) monitoring the distillate of the a short chain alcohol or emulsifier or both. In one embodiment, distillation is carried out at reduced pressure and, optionally, under inert gas.

In one embodiment, one method for making an alkyl glycerides comprises reacting a fatty alcohol and glycerine at an elevated temperature and reduced pressure in the presence of an acid catalyst, using at least 0.5 moles of glycerine, 0.25 moles of a short chain alcohol (for example, n-butyl alcohol), and 0.6 g of an acid catalyst (e.g., sulfuric acid), heating the well stirred mixture to a temperature between 75° C. to 250° C., more typically 90° C. to 200° C., more typically 100° C. to 150° C. (for example, heating to a constant temperature of 110° C.), with air or $N_2$ or any inert gas bubbling through it for greater than about 1 hrs, typically greater than about 1 ½ hours, most typically greater than about 2 hrs. 0.25 moles of n-dodecyl alcohol is added very slowly to the well stirred reaction mixture at a reduced pressure to less than about 600 mm Hg, which in another embodiment is less than about 500 mm Hg. In another embodiment, the reduced pressure is less than about 300 mm Hg. In another embodiment, the reduced pressure is less than about 100 mm Hg. In another embodiment, the reduced pressure is less than about 50 mm Hg. In another embodiment, the reduced pressure is equal to or less than about 40 mm Hg.

In one embodiment, the mixture is heated under reduced pressure until a distillate appears. Stop the reaction once the distillate stops and cool the reaction mixture.

The fatty alcohols utilized in the present invention can include alcohols containing linear or branched-chain alkyl groups having more than about 8 carbon atoms, including but not limited to octyl, nonyl, decyl, undecyl, dodecyl, tridecyl, tetradecyl, myristyl, isomyristyl, pentadecyl, cetyl, heptadecyl, stearyl, isobehenyl, octyldecyl, octyldodecyl and behenyl groups. In one embodiment, the alkyl group contains from about 8 to about 40 carbon atoms. In another embodiment, the alkyl group contains from about 8 to about 30 carbon atoms. In yet another embodiment, the alkyl group contains from about 8 to about 25 carbon atoms. In yet another embodiment, the alkyl group contains from about 10 to about 25 carbon atoms. In yet a further embodiment, the alkyl group contains from about 8 to about 22 carbon atoms.

Emulsifiers used in the present invention include but are not limited to polyoxyethylenated fatty acids, short chain fatty alcohols, polyoxyethylenated sorbitan esters, amine or polyvalent metal salts of fatty acids.

The short chain alcohols typically contain less than 7 carbon atoms, more typically less than 5 carbon atoms, more typically less than 4 carbon atoms. In one embodiment, the short chain alcohol is n-buyl alcohol. In other embodiments, the short chain alcohols include but are not limited to methyl, ethyl, propyl, isopropyl, butyl, isobutyl, s-butyl, t-butyl, pentyl, hexyl alcohols The catalyst can include acidic or alkaline catalysts. The catalyst can include acid catalyst such as stannic chloride or boron trifluoride, or basic catalysts such as alkali metals, alkali metal hydroxides, alkali metal alcoholates and tertiary amines. In one embodiment, the catalyst is chosen from organic acids, organic acid salts, inorganic acids, inorganic salts or combinations thereof.

Useful organic acids are typically those of a sulfonic acid or a carboxylic acid. Anionic counter-ions of the organic acid salts are typically sulfonates or carboxylates. Representative of such organic molecules include aromatic sulfonates and carboxylates such as p-toluene sulfonate, naphthalene sulfonate, chlorobenzoic acid, salicylic acid, phthalic acid and the like, wherein such counter-ions are water-soluble. Most preferred are salicylate, phthalate, p-toluene sulfonate, hydroxynaphthalene carboxylates, e.g. 5-hydroxy-1-napthoic acid, 6-hydroxy-1-napthoic acid, 7-hydroxy-1-napthoic acid, 1-hydroxy-2-naphthoic acid, preferably 3-hydroxy-2-naphthoic acid, 5-hydroxy-2-naphthoic acid, 7-hydroxy-2-napthoic acid, and 1, 3-dihydroxy-2-naphthoic acid and 3,4-dichlorobenzoate.

Useful inorganic salts include water-soluble potassium, sodium, and ammonium salts, such as potassium chloride and ammonium chloride. Additionally, calcium chloride, calcium bromide and zinc halide salts may also be used. Organic salts, e.g. trimethylammonium hydrochloride and tetramethylammonium chloride, may also be used.

EXAMPLE 1

Place 0.5 moles (46.0 g) of glycerin, 0.25 moles (18.5 g) of n-butyl alcohol, and 0.6 g of conc. sulfuric acid in a round-bottom 3-necked flask equipped with a thermometer, an efficient stirrer, and a gas inlet tube, leaving one flask neck open. Heat the well —stirred mixture to greater than about 90° C. With air (or nitrogen gas) bubbling through it for greater than 1 hour. Attach a condenser and attachments for reducing the pressure to about 40 mmHg.

Very slowly add 0.25 moles (46.5 g) of n-dodecyl alcohol to the well-stirred reaction mixture at the reduced pressure, and heat it to about 130° C. Look for a very small distillation of n-butyl alcohol. After all the n-dodecyl alcohol has been added, check sample of the reaction mixture for its dispersability in water and for foaming of the aqueous dispersion. Stop the reaction when dispersion and foaming appear in the aqueous dispersion. A 0.1% aqueous dispersion and foaming appear in the aqueous dispersion. A 0.1% aqueous dispersion of the reaction mixture should have a surface tension of about 29 mN/m and should foam when shaken.

A One step process using fatty alcohol and glycerine to synthesize polyglycerides of fatty alcohols will provide an approximately 100% renewable surfactant that is cost effective, efficient and completely or substantially CMR free. The synthetic methods mentioned in prior art uses hazardous chemicals as glycidyl ethers, epichlorohydrin that are listed as CMR and known carcinogens and hazardous to handle.

Accordingly, the present invention is not defined by the above description, but is to be accorded the full scope of the claims so as to embrace any and all equivalent compositions and methods.

What is claimed is:

1. A process for preparing a polyglycerol ether of fatty alcohol comprising the steps of:
   a) contacting a fatty alcohol with glycerine, in the presence of an:
      (i) acid catalyst,
      (ii) a solvent, and
      (iii) a short chain alcohol, emulsifier or a combination thereof.

2. The process of claim 1 further comprising the step of b) distilling off the short chain alcohol, emulsifier or combination thereof at reduced pressure.

3. The process of claim 2 wherein step b) is performed under an inert gas.

4. The process of claim 1 wherein the fatty alcohol has from 8 to 22 carbon atoms.

5. The process of claim 1 wherein the fatty alcohol has from 8 to 40 carbon atoms.

6. The process of claim 1 wherein the short chain alcohol has from 1 to 5 carbon atoms.

7. The process of claim 1 wherein the short chain alcohol has from 1 to 7 carbon atoms.

8. The process of claim 1 wherein the solvent is a dibasic ester, water or a combination thereof.

9. A process for preparing a polyglycerol monoether of formula:

$$R_1O\text{—}(C_3H_6O_2)_n\text{—}H \quad (1)$$

wherein $R_1$ is a $C_8$-$C_{22}$ alkyl group or hydrogen and —n— is an integer greater than 1, the process comprising the steps of:
   a) contacting a $C_8$-$C_{22}$ fatty alcohol with glycerine, in the presence of an:
      (i) acid catalyst,
      (ii) a solvent, and
      (iii) a short chain alcohol, emulsifier or a combination thereof;
   b) distilling off the short chain alcohol, emulsifier or combination thereof at reduced pressure.

10. The process of claim 9 wherein step b) is performed under an inert gas.

11. The process of claim 9 wherein the fatty alcohol has from 8 to 22 carbon atoms.

12. The process of claim 9 wherein the short chain alcohol has from 1 to 5 carbon atoms.

13. The process of claim 9 wherein the solvent is a dibasic ester, water or a combination thereof.

14. A process for preparing a polyglycerol polyether of formula:

$$R_1O\text{—}(C_3H_5O_2R_2)n\text{—}H \quad (2)$$

wherein $R_1$ and $R_2$ are individually a $C_8$-$C_{22}$ alkyl group or hydrogen and —n— is an integer greater than 1, the process comprising the steps of:

a) contacting a $C_8$-$C_{22}$ fatty alcohol with glycerine, in the presence of an:
  (i) acid catalyst,
  (ii) a solvent, and
  (iii) a short chain alcohol or emulsifier or both;
b) distilling off the short chain alcohol, emulsifier or combination thereof at reduced pressure.

15. The process of claim 14 wherein step b) is performed under an inert gas.

16. The process of claim 14 wherein the fatty alcohol has from 8 to 22 carbon atoms.

17. The process of claim 14 wherein the short chain alcohol has from 1 to 5 carbon atoms.

18. The process of claim 14 wherein the solvent is a dibasic ester, water or a combination thereof.

19. The process of claim 1 wherein the acid catalyst comprises stannic chloride or boron trifluoride.

* * * * *